United States Patent [19]
Enke et al.

[11] Patent Number: 5,175,430
[45] Date of Patent: Dec. 29, 1992

[54] TIME-COMPRESSED CHROMATOGRAPHY IN MASS SPECTROMETRY

[75] Inventors: Christie G. Enke, East Lansing; John F. Holland, Lansing; Richard D. McLane, Lansing; George E. Yefchak, Lansing, all of Mich.

[73] Assignee: Meridian Instruments, Inc., Okemos, Mich.

[21] Appl. No.: 702,221

[22] Filed: May 17, 1991

[51] Int. Cl.⁵ .................. B01D 59/44; H01J 49/00
[52] U.S. Cl. ......................... 250/282; 250/288
[58] Field of Search ............. 250/288, 281, 282

[56] References Cited

U.S. PATENT DOCUMENTS

| | | | |
|---|---|---|---|
| 4,490,806 | 12/1984 | Enke et al. | 364/734 |
| 4,807,148 | 2/1989 | Lacey | 73/23.36 |
| 4,904,872 | 2/1990 | Grix et al. | 250/287 |
| 5,015,848 | 5/1991 | Bomse et al. | 250/281 |

Primary Examiner—Bruce C. Anderson
Attorney, Agent, or Firm—Miller, Morriss & Pappas

[57] ABSTRACT

A process and apparatus employing the time compression of chromatography in mass spectrometry with array detection in which the time compressed informatioin is deconvoluted by mathematical analysis for recovery of analytical information made inaccessible in the time compression and thereby resulting in a decrease in analysis time and improved component identification without loss of sensitivity.

11 Claims, 5 Drawing Sheets

TIME-COMPRESSED CHROMATOGRAPHY IN MASS SPECTROMETRY

This invention was made with government support (Grant P41-RR-00480) awarded by the National Institutes of Health and the government has certain rights in the invention.

A process and apparatus for achieving an accelerated chromatographic analysis in which chromatography is combined with a mass spectrometer capable of high speed array detection to produce a scan time compression in the range from 50 to 200 scans per second, the column eluent transported to the mass spectrometric ion source for generation and subsequent high speed mass analysis of the ions, acquiring the mass spectral information by array detection, and processing the mass spectral information by deconvolution of overlapping chromatographic peaks, thereby compensating for the less complete separation created by the time compression and recovering information made inaccessible by time compression and a new and unobvious apparatus for actuating the process of time compression by producing data sufficient for deconvolution of analytical information with amazing time saving and with surprisingly good compound resolution and full mass range information without loss of sensitivity.

BACKGROUND

Chromatography, in modern separation science addresses the separation of components found in a mixture on the basis of their differing behavior between a moving phase and a stationary phase, which phases are in continuous and direct contact. When the moving phase is gaseous it is known as gas chromatography. Interaction with the stationary phase is of two forms; as surface adsorption, or solubility in a static liquid phase. One, (former) is called adsorption chromatography, and the other (latter) is called partition chromatography because each analyte partitions itself between the moving phase and the stationary phase by reason of its chemical nature.

In gas chromatography, the instrument utilized is a gas chromatograph which includes three general components: an inlet system; a column containing the stationary phase, and a detector. The inlet system may accommodate liquid or gaseous samples. The liquid samples are immediately volatilized in the inlet. The sample may be subsequently applied directly into the column, may be split so that only a certain portion goes to the column, or, in the case of gaseous samples, may be trapped in a stationary state and later expelled from the trap by a purging mechanism and directed into the column, again, either in total or in part.

In gas chromatography over the last 20 years the component showing the most advancement is the column, originally characterized as packed columns. The packed columns were relatively large open tubes packed with the stationary-phase-coated particles. Typically, using a carrier gas such as helium for the moving phase, a mixture containing various components was introduced onto the column where the components were separated in time so that the duration of a detected peak for each component ranged from several seconds to a few minutes. The most common detectors in original use were thermal conductivity or hydrogen flame-ionization. Both detectors were non-specific in their response and both required complete temporal separation of each of the individual components of the sample for proper analysis.

To provide additional information from each component, a two-dimensional detection system, such as a mass spectrometer was attached to the gas chromatograph. The result of this modification was the creation of a gas chromatograph/mass spectrometry GC/MS hybrid instrument. The GC/MS instrument was the first instrument requiring a computerized data system (GC/MS/DS) which became the dominant analytical instrument in modern laboratories. The typical mass spectrometer could obtain a complete mass spectrum, or scan, in about one second so as to enable numerous scans within the time frame of a single eluting peak. There followed the development of fused silica capillary columns and bonded stationary phases. Consequently, the peak widths of the gas chromatography (GC) were reduced to a few seconds, or less, creating substantial demands upon the speed and performance of the mass spectrometer.

Manufacturers of mass spectrometers attempted to accommodate the new demand for increased speed in scanning but failed to reach a performance in which no chromatographic information was lost while simultaneously maintaining adequate sensitivity. Various improvements such as magnetic sector instruments utilizing laminated magnets, smaller magnets and variant geometries attained scan speeds approaching three full mass range scans per second. One manufacturer, using a magnetic field via electromagnetic coils only, reached scan speeds up to 50 full scans per second. Such an increase in rate of scanning diminished the sensitivity of the instrument; and effective scanning with sufficient sensitivity for gas chromatographic analysis is limited to a maximum of about 10 scans per second. Quadrupole instruments designed with decreased length of the quadrupole filter and increased extraction potential attained rates of two to three s per second with reasonable sensitivity.

Time-of-flight mass spectrometry (TOFMS) has enjoyed the potential of producing mass spectra at a rate of 5,000 to 10,000 scans per second. However, used in its original embodiment, TOFMS, when combined with a data system, employs a technique known as time sliced detection (TSD) which limits this rate approximately to one full range scan per second to maintain reasonable sensitivity. In TOFMS, the ions are extracted from the ion source and are accelerated to a constant energy and are allowed to separate on the basis of the velocity (hence mass). An exact measurement in the time-of-flight over a fixed distance provides information for subsequent mass assignment. In TSD, only a small fraction of the mass range is actually measured after each extraction and this is accomplished by collecting data from a small time period, usually in the range of 2 to 20 nanoseconds wide, from each extraction. Varying the time delay between extraction and data collection for successive extraction cycles provides the information for a complete mass axis scan.

In the art described above, ions are measured as a function of their mass in a time dependent sequential manner. Since only the ions of a single mass are being measured at any given time, individual ion statistics for every mass are lost whenever other ions are being measured. Mass spectrometers that operate this way are called scanning mass spectrometers. Another means of ion measurement involves array detection. In array detection, ions throughout the mass range are measured simultaneously or sequentially from an event simultaneous to all ions. Spatial array detectors are comprised of multiple miniature ion detectors across whose dimenstions the ions are dispersed as a function of their mass. By this means, all the ions present are measured simultaneously. Readout mechanisms for this technology are cumbersome and time consuming, and to date, no applications to chromatography have been documented.

Temporal array detectors measure in the time domain either in a synchronous or a nonsynchronous manner. Synchronous detectors measure in the frequency domain while nonsynchronous detectors measure time. Simultaneous frequency detectors confine the ions in electric and magnetic fields and utilize Fourier transform techniques to detect and quantify all of the ions present at the same time. These types of array detectors have been applied to chromatography attaining 2-5 spectra per second with moderate to poor sensitivity. Another type of frequency array detector is the ion trap mass spectrometer. In this device, after an ionization event, all of the ions are trapped in an RF field. Changing the amplitude and/or frequency characteristics of the field allows the ions to be measured sequentially in mass by increasing each iso-mass orbit until a fixed ion detector is encountered. This is an example of an array detector that measures all ions subsequent to an ionization and trapping event. Spectral production rates up to 50 per second have been accomplished with this device; however, at a significant sarcifice of sensitivity and resolution. For chromatographic applications, rates in the 2 to 10 spectra per second range are more typical. The presently described unit utilizes nonsynchronized temporal array detection called time array detection (TAD). When several full mass spectra can be obtained over the time required to elute a single compound, information about the way in which the eluant composition changes with time can be realized. The ability to use these data to detect and distinguish compounds whose elution profiles overlap has been demonstrated by several early practitioners of GC/MS. One of the first publications in which this process was demonstrated and roughly described was that of J. E. Biller and K. Biemann in 1974 (7 Anal Lett 515-528). Other work followed with variations on the methods used for data analysis. R. G. Dromey and M. J. Stefik in 1976 (48 Anal Chem 1368-1375) analyzed the elution peak profile by the determination of m/z values (mass per unit change and time) contained in the spectrum of only one of the coeluting compounds. B. E. Blaisdell and C. C. Sweeley in 1980 (117 Anal Chem Acta 1) applied a curve fitting algorithm to detect and distinguish coelutants. A least squares analysis was employed by F. J. Knoor, H. R. Thorsheim and J. M. Harris in 1981 (53 Anal Chem 821) and factor analysis was used by M. A. Sharaf and B. R. Kowalski in 1982 (54 Anal Chem 1291-1296). Despite these efforts and apparent success with model examples of data sets, and despite general availability of at least one implementation of these algorithms with commercial GC/MS instruments, the technique, sometimes referred to as deconvolution, has not been significantly employed. Its lack of successful application is not due to a lack in the sophistication of the algorithms employed but rather the insufficient quality and density in the data available. Advances in chromatography which have resulted in shorter peak widths and lower eluting quantities further degraded the ability of traditional mass spectrometric detectors to provide data of sufficient quality and density for chromatographic deconvolution. Thus the art of chromatographic deconvolution was conceived before its implementation was practical. It is important to note, however, that the intention of the prior art in chromatographic deconvolution was to resolve components unresolved by normal chromatography through the use of the spectral information. Since this was not practically achievable, there was no effort given to achieve reduced analysis time. The present apparatus and process achieves reduced analysis time by compensating for an intentional reduction in chromatographic (time) resolution by deconvolution processes. Until the achievement of spectral data of sufficiently high quality and density was realized such an approach could not be anticipated. The obtention of such high quality data is a significant indicia of present invention.

Accordingly, the present invention has as its principal object an extension of TOFMS by use of procedure and apparatus for time array detection (TAD) permitting the reduction of time required for analysis by use of time compression chromatography with sensitivity and lost resolution sacrificed by temporal compression completely recovered by high density data acquisition and a deconvolution of overlapping chromatographic peaks.

Another object of the invention is to achieve the method objectives by use of available instrument components such as an integrating transient recorder which provides sufficient data to achieve mathematical deconvolution by processing mass spectral information.

Still other objectives are to extend instrumentation in mass spectral analysis for fast and sensitive usage.

Other objects in economy and simplicity and saved time in analysis will be appreciated as the description proceeds.

GENERAL DESCRIPTION

In time-array detection (TAD) all ions removed from the source after a single extraction are measured as ions of increasing mass strike the ion detector in series. The signal generated by the detector from each extraction is designated a transient. The information contained in each transient is transformed into a digital domain for subsequent storage and processing at a rate of 200 million conversions per second. Because ion extraction cycles occur on the order 5000 to 10,000 per second, it is desireable and prudent to sum successive transients in a time based registry to reduce the bandpass necessary for subsequent electronic processing and to gain the signal-to-noise enhancement of the summing process. The structure performing the summation is called an integrating transient recorder (ITR) developed by Michigan State University and is capable of summing 10 to 1000 (or more) transients prior to processing and storage. The number of successive transients to be summed in any situation is determined by the number of spectra (summed transients) required per second for adequate chromatographic reconstruction. The present process and apparatus provides adequate sensitivity for spectral generation rates up to 200 per second and greater. Essential to maximum sample utilization is the ability to continuously sum successive transients generated at up to 10,000 transients per second with no loss of information. These extremely high-density data rates in two dimensions, mass per unit charge and time (m/z), are a prerequisite for adequate deconvolution by any one of a number of deconvolution routines. Past failure of any routine to become used in GC/MS is directly related to the inadequacy of the data base and not the inappropriateness of the algorithms employed.

DRAWINGS

In the drawings:

The FIG. 1 is a schematic functional diagram of the procedural steps in the present invention and illuminates the known instrument components thereof.

The FIG. 2 is a schematic flow diagram of the interrelationship of the readily available components and their functional preferred embodiment of the present invention.

The FIG. 3 is a reconstructed chromatogram from mass spectral data over a three minute period by conventional gas chromatography/mass spectrometry in identification of the 6 compounds as indicated in practice of the invention.

SPECIFIC DESCRIPTION

Figure 1:
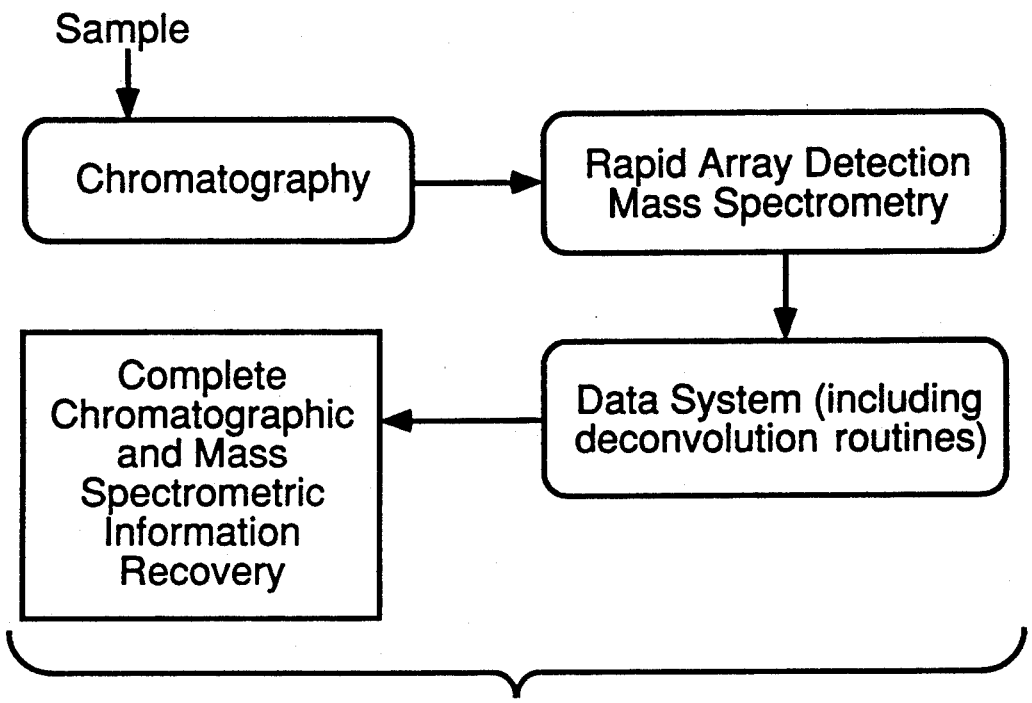
Figure 2:
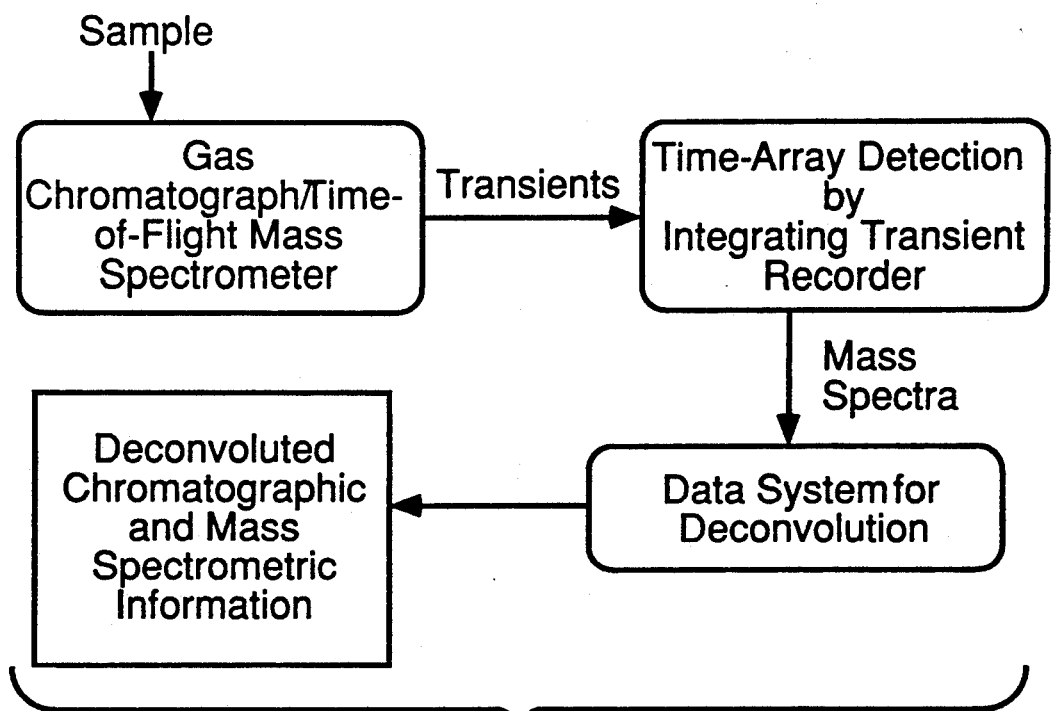
Figure 3:
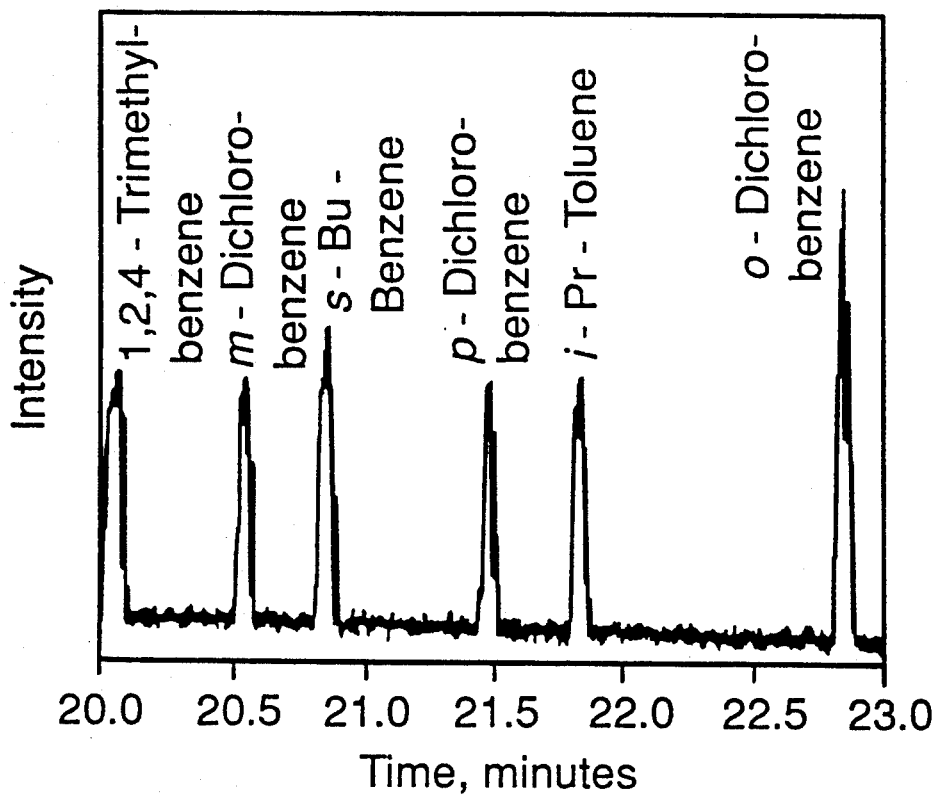
Figure 4:
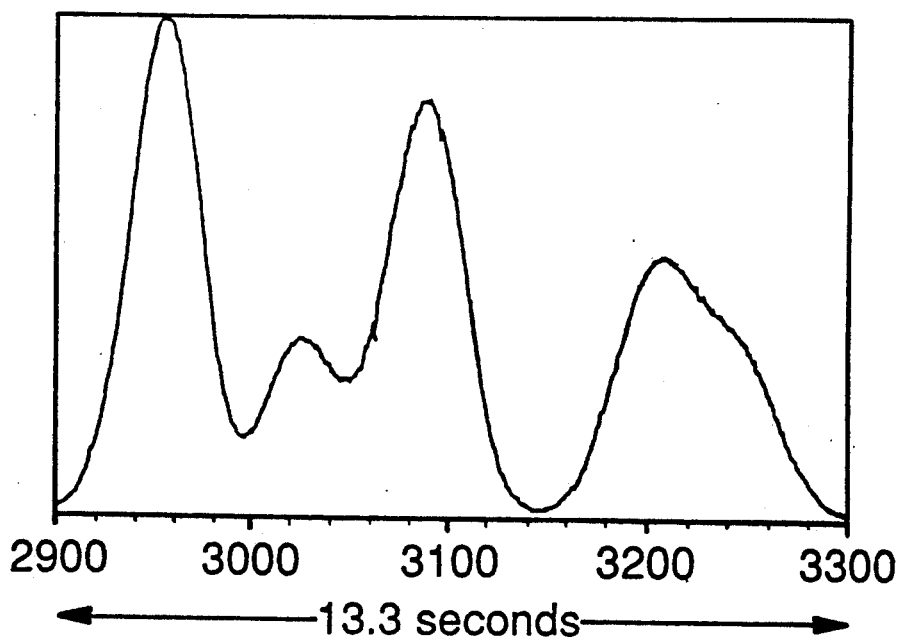
FIG. 4 is a deconvoluted reconstructed chromatogram in accord with the present invention of the same six compounds as in FIG. 3 and obtained in 13.3 seconds.
Figure 5:
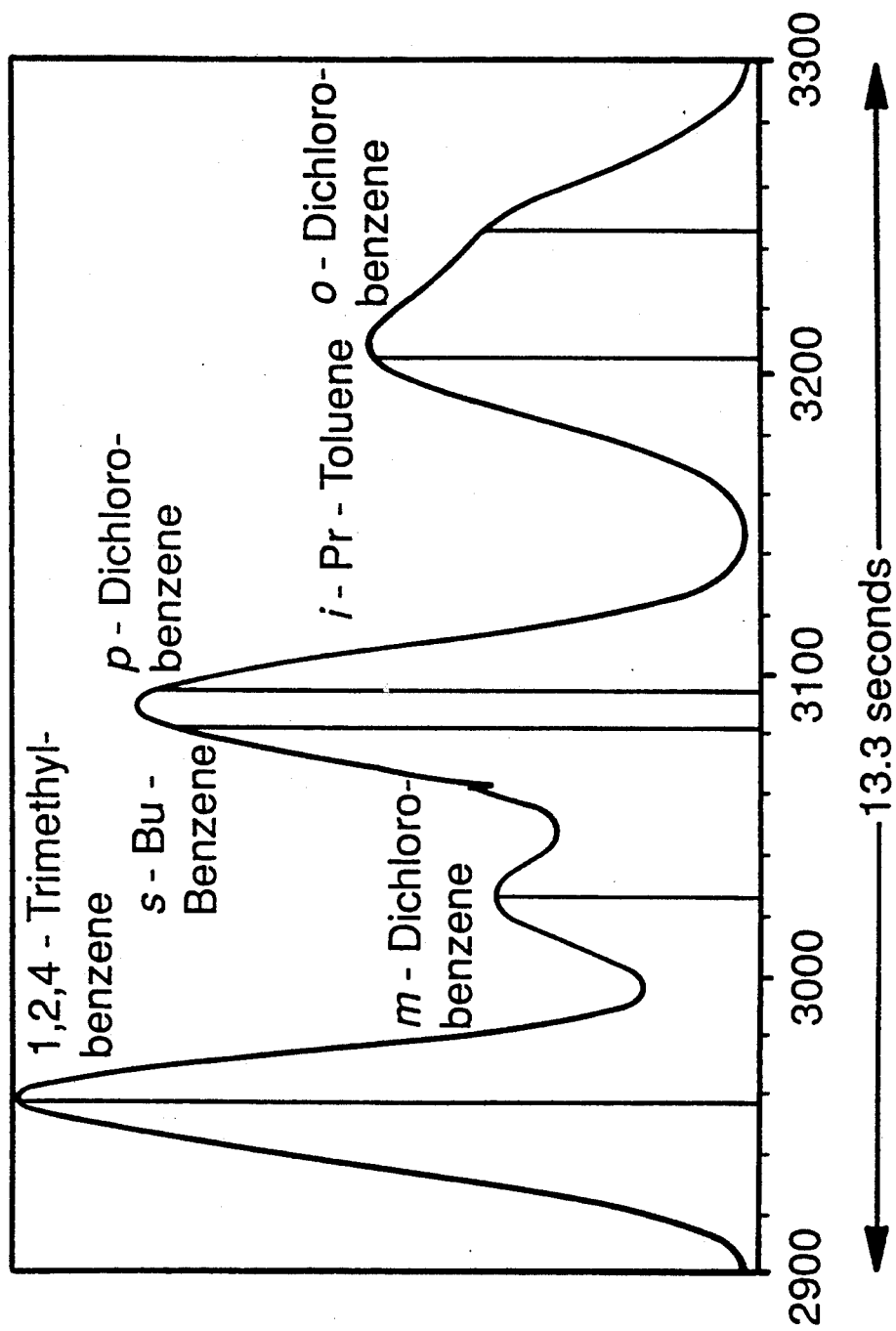
FIG. 5 is a reconstructed deconvolution of the gas chromatogram/spectrometric data of FIG. 4 and in revelation of the identity of all six compounds.
Figure 7:
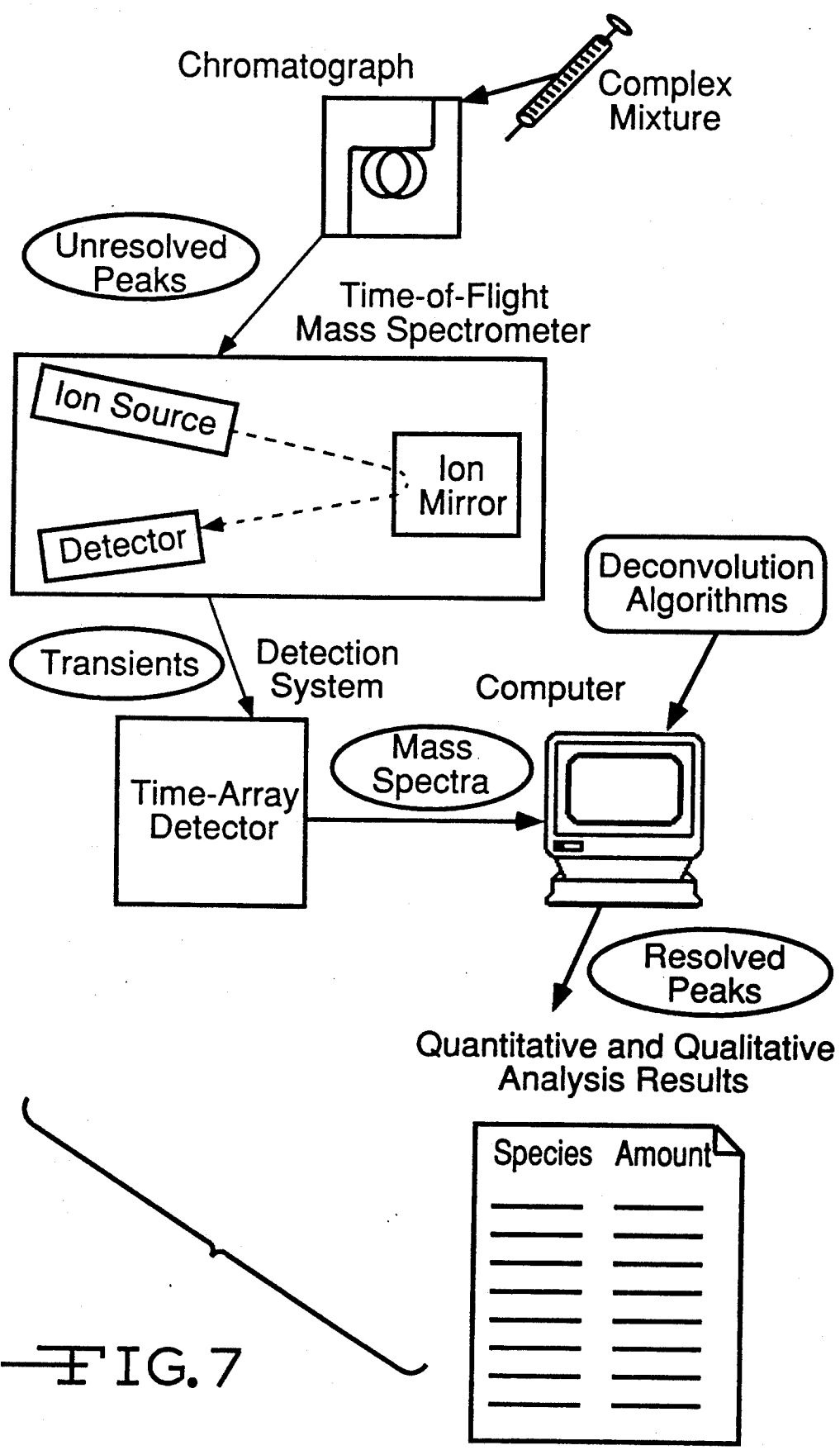
FIG. 7 is in diagramatic block form and presents the preferred configuration of the described instruments for the embodiment of time compressed chromatography to gas chromatography/mass spectrometry.

The preferred embodiment of the present invention utilizes a state-of-the art time-of-flight Mass Spectrometer (TOFMS) achieving a time-array detection (TAD) selectively as by a digital summing of successive transients and by analog integration of spectral areas in a novel manner of primary significance in revolutionizing the time domain of chromatography in which the rapid scanning is made useful by mathematical deconvolution and subsequent application of digital means in the achievement of high fidelity in the end result (FIGS. 1 and 2). The information of FIGS. 3, 4 and 5 is recovered from mass spectral data and the scan speed in the instrument in the preferred embodiment (FIG. 7) herein reported is sufficient so that no analytical information regarding the chromatographic characteristics has been sacrificed. The Mass Spectrometer furnishes a second axis of information and it is possible to discriminate between compounds that are not completely separated in time to provide a construction essential for gas chromatographic detection and application. The second axis of information when coupled with the scanning capability of time-array detection (TAD) mass spectrometry permits the time compressed chromatography. As earlier noted, this time compressed chromatography sacrifices chromatographic resolution in order to reduce the analysis time (FIG. 3). A comparison of normal and time-compressed chromatography is shown in FIGS. 3, 4 and 5. Six components of a mixture are chromatographically separated over the three-minute normal chromatogram as shown in FIG. 3 by the labeled peaks indicating their elution. When the chromatographic column is shortened and the mobile phase flow rate increased for quicker elution (a purposeful compromise of chromatographic fidelity - an essential feature of time compression), the same six compounds elute over a period of 13.3 seconds, but they are not longer chromatographically resolved (separated) as shown in FIG. 4. To illustrate the data density provided by TCC, the horizontal axis in FIG. 4 is labeled according to acquired spectrum number indicating the acquisition (by time-of-flight mass spectrometry with time-array detection) of 400 spectra over this same 13.3 second interval. The deconvolution or mathematical analysis of these high-quality, high density data reveals clearly the elution times of the six compounds and the mass spectra derived from the deconvoluted data provide positive identification. The individual component mass spectra produced by deconvolution of the TCC data in FIG. 4 exactly match those spectra produced by the conventional data in FIG. 3.

Deconvolution algorithms are based on the fact that, as a compound elutes from the chromatographic column, the intensities of all the m/z values contained in its mass spectrum will change synchronously, that is, the intensity will remain in constant proportion to one another through the raise and fall in their values. Two types of implementations of deconvolution are possible: one in which the mass spectral data are analyzed to determine the retention times, quantities, and identities of eluting compounds without incorporating any a priori knowledge of sample composition (called forward search) and one in which the quantity and retention time of specific targeted compounds are determined by detecting the appearance of their characteristic mass spectra (called reverse search).

The forward search deconvolution processes involve a series of data processing routines:

1) for making the data, stored as successive mass spectra, accessible as intensity vs. time profiles for each m/z value (called an ion chromatogram), generally by data file manipulation;

2) for determining peak positions in the individual ion chromatograms, generally by searching each ion chromatogram for the appearance of a peak and then determining the time of peak maximum or peak centroid;

3) for determining the number of compounds eluting in each section of the chromatogram, their exact retention times, and the m/z values of significant intensity in their mass spectra, generally by determining which sets of peaks identified in step 2 are mutually synchronous, allowing in the method for the possibility that some m/z values may appear in several coeluting compounds;

4) for obtaining the mass spectrum for each of the eluting compounds, generally by calculating the relative intensities of the m/z values determined to be synchronous in step 3, apportioning appropriately the intensities of m/z values shared among coelutants;

5) for determining the identity of each of the eluting compounds, generally by searching a library of mass spectra of known compounds for the mass spectra that most closely match those obtained in step 4;

6) for determining the quantity of particular eluting compounds, generally by relating the intensities of ions in the mass spectra of the unknowns with those of a known internal standard compound.

The reverse search deconvolution involves a different series of data processing routines:

1) for searching a limited range of the mass spectral data for the appearance of the spectrum of each sought compound, generally by searching for the simultaneous appearance of the major m/z values in the sought compound's mass spectrum, the range of search being determined by the temporal elution behavior of the component being sought;

2) for the confirmation of the appearance of the sought compound, generally by a goodness-of-fit test between the sample spectrum and the library standard and confirmation of the synchronicity of the intensity changes in the m/z values in the sought compound's mass spectrum;

3) for determining the quantity of the sought compounds, generally by relating the intensities of ions in the mass spectra of the sought compounds with those of a known internal standard compound;

4) for determining the elution time and elution profile of the sought compound, generally by mathematical analysis of the peak shapes of the individual ion chromatograms as determined in step 2.

Forward and reverse deconvolution algorithms can be combined in various sequences for the analysis of data from a single sample. For example, an "idealized" data set can be constructed from the amount, identity, elution profile, and library mass spectrum of each compound discovered by either forward or reverse search. This data set resulting from the identified compounds can be subtracted from the sample data set to obtain a data set containing only the unaccounted for intensities. This residual data set can then be analyzed by either forward or reverse deconvolution to determine the presence of minor or otherwise hidden compounds. Utilizing algorithmic data analysis of the mass spectra, such deconvolution can recover all of the analytical fidelity that the time compression chromatography sacrifices. The consequence, in most cases, is as seen in FIGS. 4 and 5 and the analyses of complex mixtures can be performed in less than an order of magnitude of the time than is presently feasible. Thus the FIG. 5 shows the results of the deconvolutions of the chromatogram of FIG. 4. All six compounds were identified even though the analysis occurred in less than one-thirteenth the time required for conventional gas chromatographic/mass spectral separation.

The components of the apparatus for achieving the time compressed gas chromatography and mass spectrometry are a readily available chromatograph (as a Hewlett-Packard 5890A or equivalent) for gaseous or liquid samples connected to a time-of-flight mass spectrometer available in the instrument market and a time array detector with spectral data integrated by a transient recorder device (U.S. Pat. No. 4,490,806) to a data system into which selected algorithmic analysis programs have been integrated and having an analytical capability yielding a complete deconvoluted product. The computer data system in the preferred embodiment consists of a VME bus with a Motorola 147 computer as the bus master. Three Motorola 133 microcomputers are mounted on this bus and convert the raw data scan files produced by the integrating transient recorder (ITR) into mass intensity pairs for appropriate mass spectral data processing and output. The user interface for this data system is a 386 microcomputer utilizing conventional DOS PC software. The data system is attached by an ethernet linkage to a local area network to which files can be transferred for processing and output.

The steps in the procedure utilize the equipment in the sequence or presentation above, which reduces the time in chromatographic analysis by time compression of the separation of analytes in which chromatographic resolution is compromised and transferring the column eluent into a mass spectrometer ion source (U.S. Pat. No. 4,904,872) resulting in a generation and synchronized extraction of ions from the ion source and acquiring and integrating the mass spectral information and thereafter mathematically deconvoluting the overlapping chromatographic peaks and thereby providing high quality reconstituting of the chromatographic information by deconvolution utilizing the spectral information.

Figure 6:
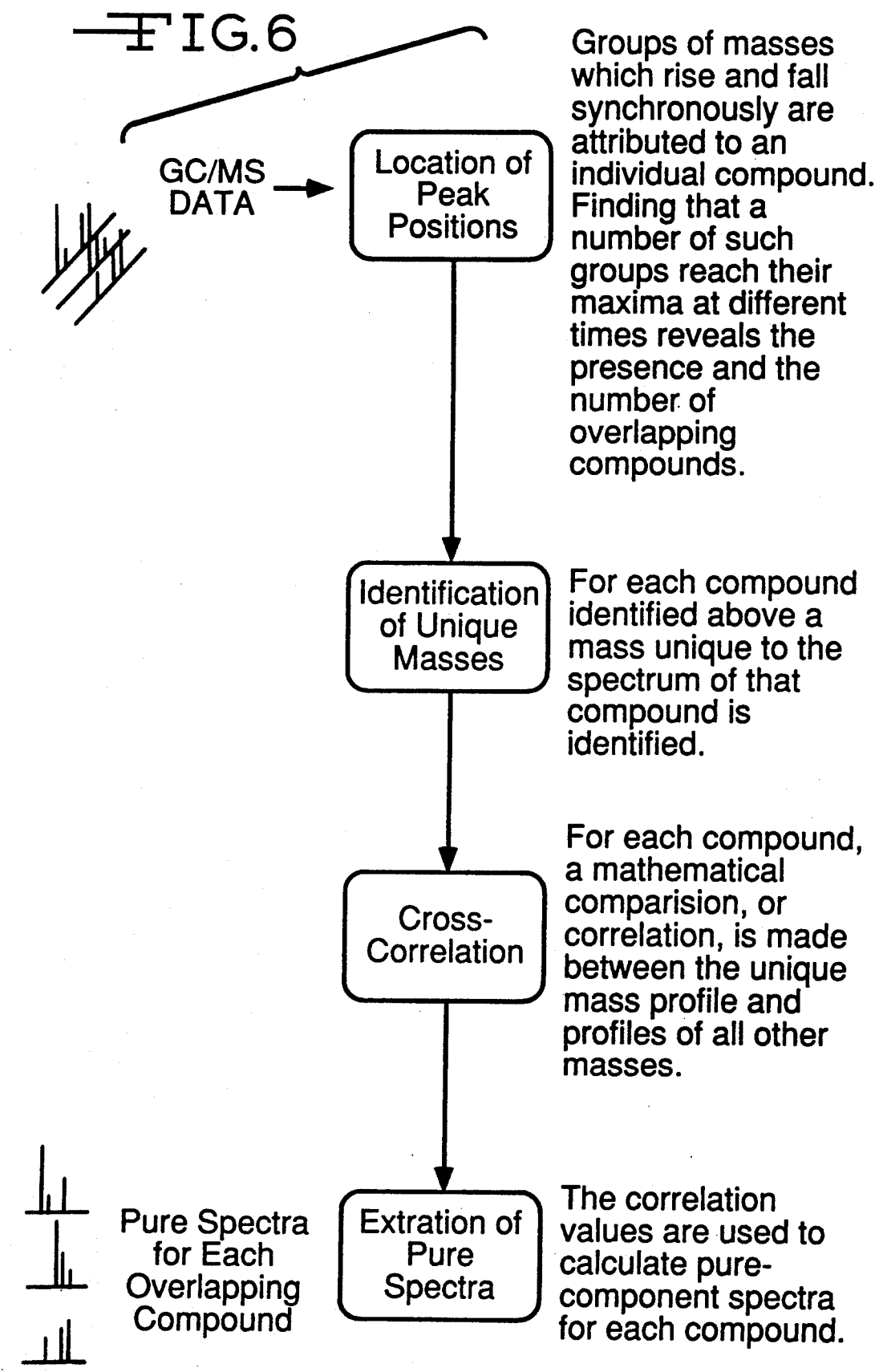
FIG. 6 is a flow chart of spectral deconvolution as expressed in the present invention and as applied to mixtures of unknown components.

The embodiment illustrated in FIG. 6 shows the deconvolution and subsequent analytical definition of mixtures of unknown compounds by forward library searching. Deconvolution appropriate to the analysis of mixtures of known compounds (targeted analysis) utilizes algorithms for reverse library searching. Both forward and reverse algorithms are used in logical sequence for complete analytical definition. Either or both are available as required.

The spectrometer preferred is one in which ions are generated and stored in an ion source and where synchronous extraction of ions for time-of-flight mass analysis is provided. Of substantial assistance is the temporal focusing of the ions over the entire mass range by an ion mirror (DE 3726952 Germany) or structure providing similar function.

Having thus described a preferred embodiment of our invention and its tested options in use, those skilled in the art of chromatography and spectrometry will readily appreciate the significance of our inventive contribution. Improvements, changes and modifications will be appreciated by those skilled in the art and it is our intent that such improvements, changes and modifications are included within the spirit of the invention and limited only by the scope of our hereinafter appended claims.

We claim:

1. A method for reducing the time required in chromatographic analyses comprising the following:
  compression in time of a chromatographic separation of analytes on a chromatographic column resulting in a loss of chromatographic resolution;
  transport of the column eluent into a mass spectrometer ion source;
  generation of ions within the ion source;
  mass analysis by rapid array detection mass spectrometry;
  acquisition and computer processing of said mass spectral information including mathematical deconvolution of overlapping chromatographic peaks; and
  said deconvolution constituting recovery of all of the chromatographic analytical information.

2. In the method of claim 1 wherein mass analysis by rapid array detection is accomplished by a time-of-flight mass spectrometer employing time array detection by use of an integrating transient recorder.

3. A method as claimed in claim 2 in which mass spectra are generated at a rate commensurate with the temporal information contained in the eluting chromatographic peaks and sufficient for deconvolution of overlapping peaks.

4. A method as claimed in claim 3 in which acquisition and integration of mass spectral information is selectively accomplished by digital summing of time-of-flight mass spectral transients and by analog integration of spectral region of interest followed by digital acquisition.

5. A method as claimed in claim 4 in which mass spectral data are processed via computerized deconvolution algorithms capable of recovering information made inaccessable by time-compression.

6. A device for time-compressed chromatography comprising:
  a chromatograph having a column and a sample inlet system;
  an interface for transporting the column eluent into a mass spectrometer ion source; a mass analyzer capable of high speed array detection;
  a data system for collection, processing, storage, and output of mass spectrometer data files;
  said processing including the execution of algorithms appropriate for the mathematical deconvolution of overlapping chromatographic peaks;
  means to compress said peaks in time whereby losses in resolution produced by said time compression are recovered by the mathematical deconvolution resident in and executed by said data system.

7. A device as in claim 6 wherein chromatographic separation of analytes is performed in a chromatograph such as a Hewlett-Packard 5890-A gas chromatograph and a time-of-flight spectrometer employing a time array detector by means of an integrating transient recorder.

8. A device as in claim 6 wherein a data system capable of sufficient data transfer rates and processing speed collects, processes, stores and outputs mass spectral data; said processing including the execution of deconvolution algorithms appropriate for the mathematical deconvolution of overlapping chromatographic peaks.

9. A device as in claim 8 wherein ions are generated and stored in an ion source capable of synchronous extraction of ions for time-of-flight mass analysis.

10. A device as in claim 8 wherein ions are mass-analyzed by time-of-flight mass spectrometry; said ions being temporally focused over the entire mass range of interest by use of an ion mirror or other means.

11. A device as in claim 10 wherein ion signals are measured by means of a detector, such as a multi-channel plate detector, capable of nanosecond-range time response and providing a large dynamic range.

* * * * *

UNITED STATES PATENT AND TRADEMARK OFFICE
CERTIFICATE OF CORRECTION

PATENT NO. : 5,175,430 C1
APPLICATION NO. : 90/007629
DATED : August 5, 2008
INVENTOR(S) : Christie G. Enke et al.

Page 1 of 1

It is certified that error appears in the above-identified patent and that said Letters Patent is hereby corrected as shown below:

Column 2, claim 23, line 37, "claim 24" should be --claim 6--.

Column 3, claim 39, line 52, "claim 44" should be --claim 38--.

Column 4, claim 44, line 2, after "a" insert --mass--.

Column 4, claim 48, line 10, after "a" insert --mass--.

Signed and Sealed this

Twenty-fifth Day of November, 2008

JON W. DUDAS
*Director of the United States Patent and Trademark Office*

(12) EX PARTE REEXAMINATION CERTIFICATE (6337th)
United States Patent
Enke et al.

(10) Number: US 5,175,430 C1
(45) Certificate Issued: Aug. 5, 2008

(54) TIME-COMPRESSED CHROMATOGRAPHY IN MASS SPECTROMETRY

(75) Inventors: Christie G. Enke, East Lansing, MI (US); John F. Holland, Lansing, MI (US); Richard D. McLane, Lansing, MI (US); George E. Yefchak, Lansing, MI (US)

(73) Assignee: Leco Corporation, St. Joseph, MI (US)

Reexamination Request:
No. 90/007,629, Jul. 13, 2005

Reexamination Certificate for:
Patent No.: 5,175,430
Issued: Dec. 29, 1992
Appl. No.: 07/702,221
Filed: May 17, 1991

(51) Int. Cl.
*G01N 30/00* (2006.01)
*G01N 30/72* (2006.01)
*G01N 30/86* (2006.01)
*G06F 17/00* (2006.01)
*B01D 59/44* (2006.01)

(52) U.S. Cl. .................................. 250/282; 250/288
(58) Field of Classification Search .................. None
See application file for complete search history.

(56) References Cited

U.S. PATENT DOCUMENTS

| | | |
|---|---|---|
| 4,018,241 A | 4/1977 | Sodal et al. |
| 4,178,507 A | 12/1979 | Brunnee et al. |
| 4,207,465 A | 6/1980 | Favre et al. |
| 4,540,884 A | 9/1985 | Stafford et al. |
| 4,594,506 A | 6/1986 | Ghaderi |
| 4,650,999 A | 3/1987 | Fies, Jr. et al. |
| 4,667,100 A | 5/1987 | Lagna |
| 4,694,168 A * | 9/1987 | Le Beyec et al. ............ 250/287 |
| 4,733,073 A | 3/1988 | Becker et al. |
| 4,778,993 A | 10/1988 | Waugh |
| 4,797,554 A | 1/1989 | Blanchard et al. |
| 4,837,434 A | 6/1989 | James |
| 4,847,493 A | 7/1989 | Sodal et al. |
| 4,855,594 A | 8/1989 | Kimock et al. |
| 4,861,987 A | 8/1989 | Devienne |
| 4,866,270 A | 9/1989 | Hall et al. |
| 4,870,276 A | 9/1989 | Lindinger |
| 4,889,987 A | 12/1989 | Gruen et al. |
| 4,894,536 A | 1/1990 | Conzemius |
| 4,916,313 A | 4/1990 | Hall et al. |
| 4,935,624 A | 6/1990 | Henion et al. |
| 4,941,101 A * | 7/1990 | Crilly .......................... 702/32 |
| 4,960,991 A | 10/1990 | Goodley et al. |
| 4,973,840 A | 11/1990 | Srivastava |
| 4,975,576 A | 12/1990 | Federer et al. |
| 4,996,423 A | 2/1991 | Hanna |

FOREIGN PATENT DOCUMENTS

| | | |
|---|---|---|
| EP | 0298608 | 1/1989 |
| JP | 57 17855 | 1/1982 |
| JP | 62 85850 | 4/1987 |
| JP | 63 151851 | 6/1988 |
| WO | 83 04187 | 12/1983 |

OTHER PUBLICATIONS

Page1 of website located at URL, http://pubs3.acs.org/acs/journals/toc.page?incoden=ancham&indecade=1&involume=62&inissue=10.*

Eric D. Erickson, et al., "Application of Time Array Detection to Capillary Column Gas Chromatography/Conventional Time–of–Flight Mass Spectrometry" Analytical Chemistry, 62(10), pp. 1079–1084, published May 15, 1990.*

(Continued)

*Primary Examiner*—Erik Kielin

(57) ABSTRACT

A process and apparatus employing the time compression of chromatography in mass spectrometry with array detection in which the time compressed informatioin is deconvoluted by mathematical analysis for recovery of analytical information made inaccessible in the time compression and thereby resulting in a decrease in analysis time and improved component identification without loss of sensitivity.

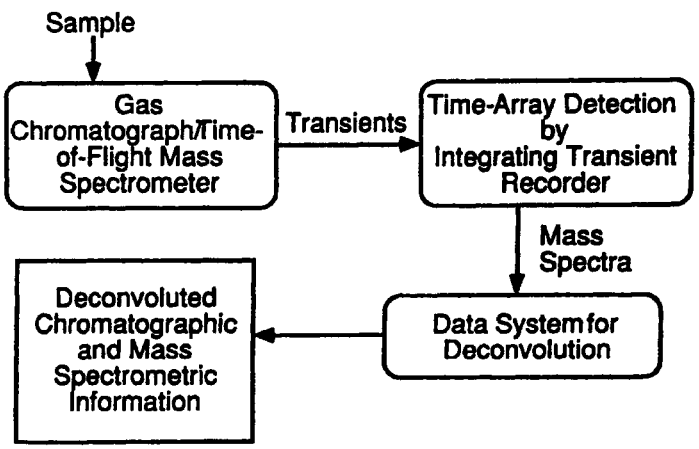

OTHER PUBLICATIONS

Karjalainen, Erkki J., "Computer–Enhanced Analytical Spectroscopy," Ed. Henk L. C. Meuz laar, vol. 2, Chap. 3, Feb. 1990, pp. 49–70.

Karjalainen, Erkki J. et al., "Mathematical Chromatography—Resolution of Overlapping Spectra in GC–MS," Medical Informatics Europe 85, Proceedings, 1985, pp. 572–578.

Synovec, R.E. et al., "New Directions in Process Liquid Chromatography," American Laboratory, Oct. 1989, pp. 82–87.

Holland, John F. et al., "Mass Spectrometry on the Chromatographic Time Scale: Realistic Expectations," Anal. Chem., 1983.

Lawton, William H. et al., "Self Modeling Curve Resolution," Technometrics, vol. 13, No. 3, Aug. 1997, pp. 617–633.

Biller, J.E. et al., "Reconstructed Mass Spectra, a Novel Approach for the Utilization of Gas Chromatograph—Mass Spectrometer Data," Analytical Letters, 7(7), 1974, pp. 515–528.

Sharaf, M. A. et al., "Quantitative Resolution of Fused Chromatographic Peaks in Gas Chromatography/Mass Spectrometry," Anal. Chem., 54, 1982, pp. 1291–1296.

Osten, David W. et al., "Multivariate Curve Resolution in Liquid Chromatography," Anal. Chem., 56, 1984, pp. 991–995.

Borgen, Odd S. et al., "An Extension of the Multivariate Component–Resolution Method to Three Components," Analytica Chimica Acta, 174, 1985, pp. 1–26.

Lacey, Richard F., "Deconvolution of Overlapping Chromatographic Peaks," Anal. Chem., 58, 1986, pp. 1404–1410.

Ghosh, Amit et al., "Differential Gas Chromatographic Mass Spectrometry," Anal. Chem., 61, 1989, pp. 73–77.

Smilde, A.K. et al., "Introduction of Multi–criteria Decision Making in Optimization Procedures for High–Performance Liquid Chromatographic Separations," Journal of Chromatography, 369, 1986, pp. 1–10.

Ramos, L. Scott et al., "Third–order Chromatography: Multivariate Analysis of Data from Parallel–column Chromatography with Multichannel Detection," Anal. Chem., 57, 1985, pp. 2620–2625.

Olive, Joaquim et al., "Resolution of Overlapping Peaks in Gas and Liquid Chromatography," Analytica Chimica Acta, 219, 1989, pp. 257–272.

Prazen, B.J., "Second–order Chemometric Standardization for High–speed Hyphenated Gas Chromatography: Analysis of GC/MS and Comprehensive GC × GC Data," J. Microcolumn Separations, 11, 1998, pp. 97–107.

Allison, J. et al., "GC/MS By Time–of–flight Mass Spectrometry: Instrumentation and Data Systems Developments," Anal. Instrum., 1987, vol. 16, pp. 207–224.

Patent Abstracts of Japan Publication No. 62–085850, Apr. 20, 1987.

Patent Abstracts of Japan Publication No. 63–151851, Jun. 24, 1988.

Pinkston, J.D. et al., "New Time–of–flight Mass Spectrometer for Improved Mass Resolution, Versatility, and Mass Spectrometry/Mass Spectrometry Studies," Rev. Sci. Instrum., 1986, vol. 57, pp. 583–592.

Yetchak, G.E. et al., "Models for Mass–Independent Space and Energy Focusing in Time–of–flight Mass Spectrometry," Int. J. Mass Spectrom. Ion Processes, 1989, vol. 87, pp. 313–330.

Studier, M.H., "Continuous Ion Source for a Time–of–flight Mass Spectrometer," Rev. Sci. Instrum., 1963, vol. 34, pp. 1367–1370.

Wiley, W.C. et al., "Time–of–flight Mass Spectrometer with Improved Resolution," Rev. Sci. Instrum., 1955, vol. 26, pp. 1150–1157.

Ingle, J.D. et al., Spectrochemical Analysis, Prentice–Hall, Englewood Cliffs, NJ, 1988, pp. 159–161.

Chesler, S.N. et al., "Effect of Peak Sensing and Random Noise on the Precision and Accuracy of Statistical Moment Analyses from Digital Chromatographic Data," Anal. Chem., 1971, vol. 43, p. 1922.

Holzer, G. et al., "Recent Advances Toward the Detection of Accelerants in Arson Cases," Am. Lab. Dec. 1988, pp. 15–19.

Lanning, L.A. et al., "Electrically Heated Cold Trap Inlet System for Computer–controlled High–speed Gas Chromatography," Anal. Chem., 1988, vol. 60, pp. 1994–1996.

Knorr, F.J. et al., "Multichannel Detection and Numerical Resolution of Overlapping Chromatographic Peaks," Anal. Chem. 1981, vol. 53, pp. 821–825.

Davis, Joe M., "Statistical Theory of Component Overlap in Multipcomponent Chromatograms," Anal. Chem., 1983, vol. 55, pp. 418–424.

Willett, J.E., "Gas Chromatography," Analytical Chemistry by Open Learning, 1987, p. 177.

Davis, Reg et al., "Mass Spectrometry," Analytical Chemistry by Open Learning, 1987, pp. 390–392.

\* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 6 are determined to be patentable as amended.

Claims 2–5 and 7–11, dependent on an amended claim, are determined to be patentable.

New claims 12–63 are added and determined to be patentable.

1. A method for reducing the time required in chromatographic analyses comprising the following:
   compression in time of a chromatographic separation of analytes on a chromatographic column resulting in a loss of chromatographic resolution *within a column eluent*;
   transport of the column eluent into a mass spectrometer ion source;
   generation of ions *from the column eluent* within the ion source;
   mass analysis *of the ions* by rapid array detection mass spectrometry *to produce mass spectra*;
   acquisition and computer processing of said mass [spectral information] *spectra* including mathematical deconvolution of overlapping chromatographic peaks *as represented in said mass spectra*; and
   said deconvolution constituting recovery of all of the chromatographic analytical information *put at risk as a result of the loss of resolution, and wherein the step of compression in time includes the compression of said chromatographic peaks such that the time of chromatographic separation is purposefully compressed to minimize elution times which causes co-elution of three or more compounds that simultaneously contribute to a mass spectrum obtained by the mass analysis at any particular instant in time.*

6. A device for time-compressed chromatography comprising:
   a chromatograph having a column and a sample inlet system, *said chromatograph producing a column eluent*;
   an interface for transporting the column eluent into a mass spectrometer ion source;
   a mass analyzer capable of high speed array detection;
   a data system for collection, processing, storage, and output of mass spectrometer data files *that create mass spectra*;
   said processing including the execution of algorithms appropriate for the mathematical deconvolution of overlapping chromatographic peaks *as represented in said mass spectra*;
   means to compress said peaks in time whereby [losses in] all of the chromatographic analytical information put at risk as a result of the loss of *resolution produced by said time compression are recovered by the mathematical deconvolution resident in and executed by said data system*, *wherein said means to compress said peaks in time compresses said peaks such that the time of chromatographic separation is purposefully compressed to minimize elution times which causes co-elution of three or more compounds that simultaneously contribute to a mass spectrum obtained from said data system at any particular instant in time.*

12. *A device as in claim 6 wherein said mass analyzer is a mass spectrometer.*

13. *A device as in claim 12 wherein said mass spectrometer is a time-of-flight mass spectrometer.*

14. *A device as in claim 13 wherein said time-of-flight mass spectrometer includes an ion mirror.*

15. *A device as in claim 12 wherein said mass spectrometer is a Fourier Transform mass spectrometer.*

16. *A device as in claim 12 wherein said mass spectrometer comprises a magnetic sector.*

17. *A device as in claim 6 wherein said mass analyzer is an ion trap.*

18. *A device as in claim 6 wherein said chromatograph is a gas chromatograph.*

19. *A device as in claim 6 wherein said sample inlet system of said chromatograph is configured to receive a gaseous sample.*

20. *A device as in claim 6 wherein said sample inlet system of said chromatograph is configured to receive a liquid sample.*

21. *A device as in claim 6 wherein said mass analyzer comprises a time array detector.*

22. *A device as in claim 6 wherein said data system comprises an integrating transient recorder.*

23. *A device as in claim 24 wherein said data system is capable of summing 10 or more transients prior to processing and storage.*

24. *A device as in claim 23 wherein said mass analyzer generates mass spectra at a rate of more than 10 spectra per second.*

25. *A device as in claim 6 wherein said mass analyzer is a time-of-flight mass spectrometer and wherein ions are extracted in said mass analyzer at a rate of 5,000 to 10,000 cycles per second.*

26. *A device as in claim 6 wherein said mass analyzer is a time-of-flight mass spectrometer that generates transients at a rate of 5,000 to 10,000 transients per second.*

27. *A device as in claim 26 wherein said mass analyzer is a time-of-flight mass spectrometer and wherein said data system is capable of summing 10 to 1,000 transients prior to processing and storage.*

28. *A device as in claim 27 wherein said mass analyzer generates mass spectra at a rate of more than 10 spectra per second.*

29. *A device as in claim 6 wherein said mass analyzer is a time-of-flight mass spectrometer that generates mass spectra at a rate of at least 200 spectra per second.*

30. *A method as claimed in claim 1, wherein the mass analysis by rapid array detection mass spectrometry includes analyzing ions from the ion source using a mass spectrometer having a time array detector.*

31. *A method as claimed in claim 1, wherein the mass analysis by rapid array detection mass spectrometry includes analyzing ions from the ion source using a time-of-flight mass spectrometer.*

32. A method as claimed in claim 1, wherein the mass analysis by rapid array detection mass spectrometry includes analyzing ions from the ion source using a Fourier Transform mass spectrometer.

33. A method as claimed in claim 1, wherein the mass analysis by rapid array detection mass spectrometry includes analyzing ions from the ion source using a mass spectrometer comprising a magnetic sector.

34. A method as claimed in claim 1, wherein the mass analysis by rapid array detection mass spectrometry includes analyzing ions from the ion source using an ion trap.

35. A method as claimed in claim 1, wherein the mass analysis by rapid array detection is accomplished by use of an integrating transient recorder.

36. A method as claimed in claim 1 wherein the acquisition and computer processing of mass spectral information is selectively accomplished by summing of mass spectral transients and by integration of a spectral region of interest followed by acquisition.

37. A method as claimed in claim 1, wherein said mass analysis generates mass spectra at a rate of more than 10 spectra per second.

38. A device for time-compressed chromatography comprising:
   a chromatograph having a column and a sample inlet system, said chromatograph producing a column eluent;
   an interface for transporting the column eluent into a mass spectrometer ion source;
   a mass analyzer capable of high speed array detection, wherein said mass analyzer generates mass spectra at a rate of more than 10 spectra per second;
   a data system for collection, processing, storage, and output of mass spectrometer data files;
   said processing including the execution of algorithms appropriate for the mathematical deconvolution of overlapping chromatographic peaks as represented in said mass spectra; and
   means to compress said peaks in time whereby all of the chromatographic analytical information put at risk as a result of the loss of resolution produced by said time compression are recovered by the mathematical deconvolution resident in and executed by said data system, wherein said means to compress said peaks in time compresses said peaks such that the time of chromatographic separation is purposefully compressed to minimize elution times which causes co-elution of three or more compounds that simultaneously contribute to a mass spectrum obtained from said mass analyzer at any particular instant in time.

39. A device as in claim 44 wherein said data system is capable of summing 10 or more transients prior to processing and storage.

40. A device as in claim 38 wherein ions are extracted in said mass analyzer at a rate of 5,000 to 10,000 cycles per second.

41. A device as in claim 38 wherein said mass analyzer is a time-of-flight mass spectrometer that generates transients at a rate of 5,000 to 10,000 transients per second.

42. A device as in claim 41 wherein said mass analyzer is a time-of-flight mass spectrometer and wherein said data system is capable of summing 10 to 1,000 transients prior to processing and storage.

43. A device as in claim 38 wherein said mass analyzer is a time-of-flight mass spectrometer that generates mass spectra at a rate of at least 200 spectra per second.

44. A device as in claim 38 wherein said mass analyzer is a spectrometer.

45. A device as in claim 44 wherein said mass spectrometer is a time-of-flight mass spectrometer.

46. A device as in claim 45 wherein said time-of-flight mass spectrometer includes an ion mirror.

47. A device as in claim 44 wherein said mass spectrometer is a Fourier Transform mass spectrometer.

48. A device as in claim 44 wherein said mass spectrometer is a spectrometer comprising a magnetic sector.

49. A device as in claim 38 wherein said mass analyzer is an ion trap.

50. A device as in claim 38 wherein said chromatograph is a gas chromatograph.

51. A device as in claim 38 wherein said mass analyzer comprises a time array detector.

52. A device as in claim 38 wherein said data system comprises an integrating transient recorder.

53. A device as in claim 38 wherein said mass analyzer is a time-of-flight mass spectrometer including an ion mirror and a time array detector.

54. A device for time-compressed chromatography comprising:
   a gas chromatograph having a column and a sample inlet system, said chromatograph producing a column eluent;
   an interface for transporting the column eluent into a mass spectrometer ion source;
   a mass analyzer capable of high speed array detection, said mass analyzer comprising a time-of-flight mass spectrometer for receiving ions from said mass spectrometer ion source;
   a data system for collection, processing, storage, and output of mass spectrometer data files that create mass spectra;
   said processing including the execution of algorithms appropriate for the mathematical deconvolution of overlapping chromatographic peaks as represented in said mass spectra;
   means to compress said peaks in time whereby all of the chromatographic analytical information put at risk as a result of the loss of resolution produced by said time compression are recovered by the mathematical deconvolution resident in and executed by said data system, wherein said means to compress said peaks in time compresses said peaks such that the time of chromatographic separation is purposefully compressed to minimize elution times which causes co-elution of three or more compounds that simultaneously contribute to a mass spectrum obtained from said data system at any particular instant in time.

55. A device as in claim 54 wherein said time-of-flight mass spectrometer includes an ion mirror.

56. A device as in claim 54 wherein said mass analyzer comprises a time array detector.

57. A device as in claim 54 wherein said data system comprises an integrating transient recorder.

58. A device for time-compressed chromatography comprising:
   a chromatograph having a column and a sample inlet system, said chromatograph producing a column eluent;
   an interface for transporting the column eluent into a mass spectrometer ion source;
   a mass analyzer comprising a time-of-flight mass spectrometer for receiving ions from said mass spectrometer ion source, said time-of-flight mass spectrometer comprising an ion mirror and a time array detector capable of high speed array detection;

a data system coupled to said time array detector for collection, processing, storage, and output of mass spectrometer data files that create mass spectra;

said processing including the execution of algorithms appropriate for the mathematical deconvolution of overlapping chromatographic peaks as represented in said mass spectra; and means to compress said peaks in time whereby all of the chromatographic analytical information put at risk as a result of the loss of resolution produced by said time compression are recovered by the mathematical deconvolution resident in and executed by said data system, wherein said means to compress said peaks in time compresses said peaks such that the time of chromatographic separation is purposefully compressed to minimize elution times which causes co-elution of three or more compounds that simultaneously contribute to a mass spectrum obtained from said data system at any particular instant in time.

59. A device as in claim 58 wherein said chromatograph is a gas chromatograph.

60. A device as in claim 58 wherein said sample inlet system of said chromatograph is configured to receive a gaseous sample.

61. A device as in claim 58 wherein said sample inlet system of said chromatograph is configured to receive a liquid sample.

62. A device as in claim 58 wherein said data system comprises an integrating transient recorder.

63. A device for time-compressed chromatography comprising:

a gas chromatograph having a column and a sample inlet system, said chromatograph producing a column eluent;

an interface for transporting the column eluent into a mass spectrometer ion source;

a mass analyzer comprising a time-of-flight mass spectrometer for receiving ions from said mass spectrometer ion source, said time-of-flight mass spectrometer comprising an ion mirror and a time array detector capable of high speed array detection;

a data system comprising an integrating transient recorder coupled to said time array detector for collection, processing, storage, and output of mass spectrometer data files that create mass spectra;

said processing including the execution of algorithms appropriate for the mathematical deconvolution of overlapping chromatographic peaks as represented in said mass spectra, wherein said processing includes the execution of algorithms approriate for the mathematical deconvolution of at least three chromatographic peaks that overlap at a given instant in time; and means to compress said peaks in time whereby all of the chromatographic analytical information put at risk as a result of the loss of resolution produced by said time compression are recovered by the mathematical deconvolution resident in and executed by said data system, wherein said means to compress said peaks in time compresses said peaks such that the time of chromatographic separation is purposefully compressed to minimize elution times which causes co-elution of three or more compounds that simultaneously contribute to a mass spectrum obtained from said data system at any particular instant in time.

* * * * *